United States Patent [19]
Doody

[11] Patent Number: 5,546,963
[45] Date of Patent: Aug. 20, 1996

[54] SURGICAL HAND AND ARM PROTECTOR

[76] Inventor: Michael C. Doody, 408 North Line St., Metairie, La. 70005

[21] Appl. No.: 267,832

[22] Filed: Jun. 28, 1994

Related U.S. Application Data

[63] Continuation of Ser. No. 46,627, Apr. 13, 1993, abandoned.

[51] Int. Cl.$^6$ ............................................. A61F 5/37
[52] U.S. Cl. ........................................ 128/878; 128/879
[58] Field of Search ........................................ 128/877, 878, 128/879, 881; 602/20, 21, 51, 62, 64, 65; 2/171

[56] References Cited

U.S. PATENT DOCUMENTS

| | | | |
|---|---|---|---|
| 826,648 | 7/1906 | Challenger | 128/878 |
| 853,025 | 4/1907 | McCalmont | 128/879 |
| 973,330 | 10/1910 | Wood | 128/879 |
| 1,227,700 | 5/1917 | Tucker | 602/21 |
| 1,561,400 | 11/1925 | Begg | 128/881 |
| 2,043,153 | 6/1936 | Cox | 128/879 |
| 2,237,252 | 4/1941 | Longfellow | 602/20 |
| 3,176,683 | 4/1965 | Posey | 128/879 |
| 3,182,657 | 5/1965 | Zurbuchen | 128/879 |
| 3,415,244 | 12/1968 | Block | 128/879 |
| 3,476,108 | 11/1969 | Matukas . | |
| 3,774,242 | 11/1973 | Owen | 602/21 |
| 3,818,905 | 6/1974 | Lebold | 602/21 |
| 4,628,911 | 12/1986 | Bornstein . | |
| 4,671,267 | 6/1987 | Stout | 602/51 |
| 4,887,616 | 12/1989 | Baijnath . | |
| 4,982,744 | 1/1991 | Stanec . | |
| 5,031,641 | 7/1991 | Upton | 128/878 |
| 5,069,203 | 12/1991 | Anderson | 602/21 |
| 5,140,998 | 8/1992 | Vickers . | |
| 5,160,314 | 11/1992 | Peters | 602/64 |
| 5,205,812 | 4/1993 | Wasserman | 128/878 |
| 5,230,351 | 7/1993 | Nyorkor | 128/878 |

*Primary Examiner*—Michael A. Brown
*Attorney, Agent, or Firm*—Pravel, Hewitt, Kimball & Krieger

[57] ABSTRACT

A surgical hand and arm protector and method of protection wherein a base is attached to an elongated arm channel terminating in a mitt; the base is placed under a patient on an operating table with a portion of the arm placed in the arm channel and the hand in the mitt.

5 Claims, 1 Drawing Sheet

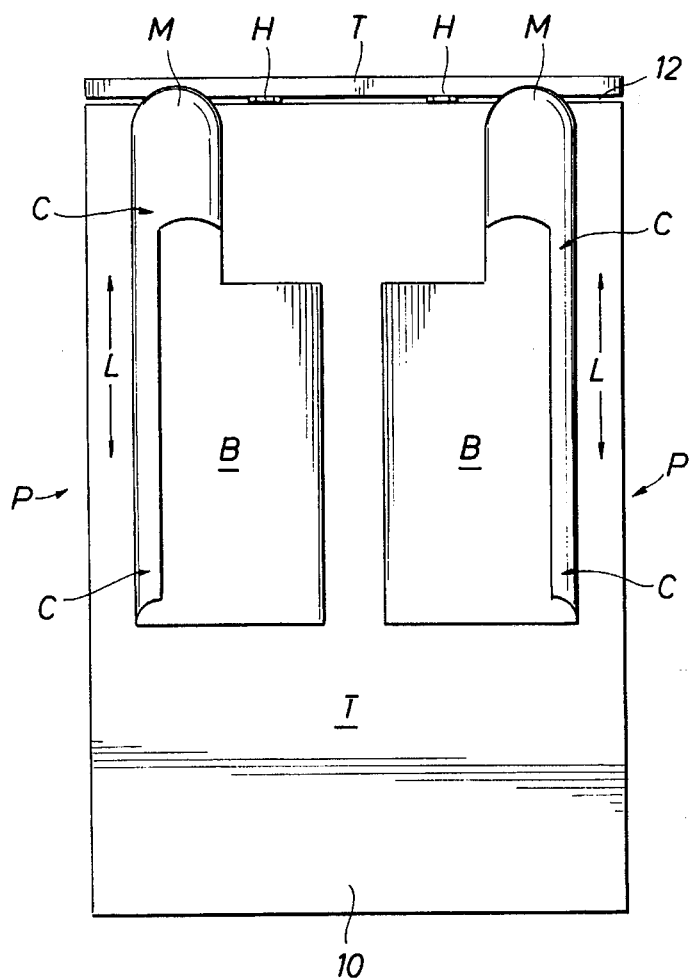
FIG.1
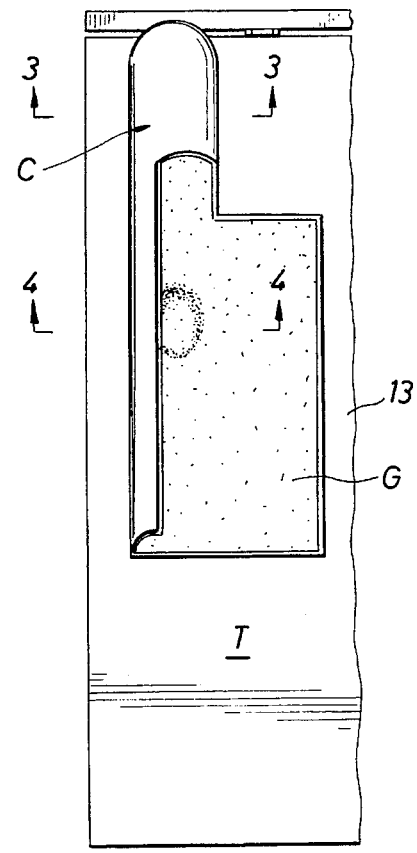
FIG.2
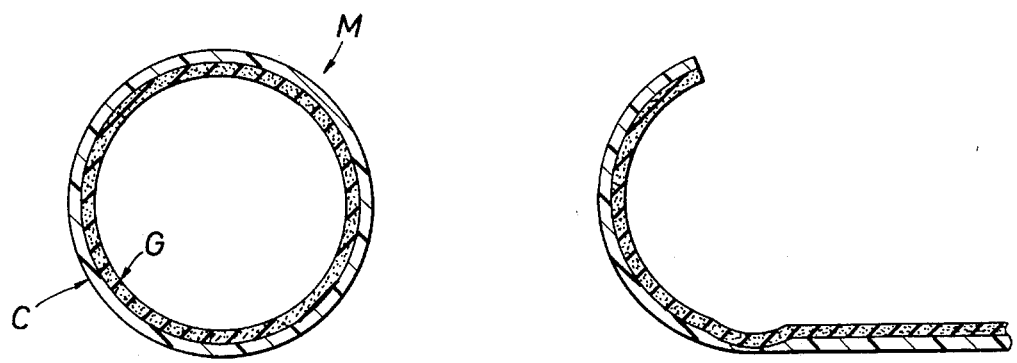
FIG.3
FIG.4

SURGICAL HAND AND ARM PROTECTOR

This is a continuation of application Ser. No. 08/046,627 filed on Apr. 13, 1993 now abandoned.

FIELD OF INVENTION

The present invention relates to a surgical hand and arm protector, particularly applicable during pelvic laparoscopy, laparotomy, cystoscopy, colorectal, and vulvovaginal surgery.

BACKGROUND OF THE INVENTION

There exists a need for a proper surgical hand and arm protector and a proper method of protection in order to keep a patient's arms at the patient's side during pelvic laparoscopy, laparotomy, cystoscopy, colorectal, and vulvovaginal surgery. The need also exists to protect the patient from hand injury, ulnar nerve compression, interference with IV lines and a loosening of pulse oximetry wires.

Although a patient's arms can be extended out to the side during laparoscopic work on the upper abdomen, pelvic surgery requires that the hands be placed along the patient's side so that the surgeon has room to stand and work. The arms are usually tucked into sheets that are then tucked under the patient's back. This comprises a clumsy and awkward method and apparatus for getting the patient ready for surgery. When the patient's arms are extended outward from the body for surgery, there exists a chance of brachial plexus injury due to stretching, so that a side-of-the-body arm placement would be preferable if it were safe for the hands and fingers.

The patients are usually in lithotomy position for the above mentioned procedures, with the bottom of the bed hinged downward. The hinge of the table usually occurs where the patient's hand normally rests at the patient's side. There are multiple instances in which patients' hands and fingers have been mangled or even amputated when the table was straightened out at the end of the case. A positive step to prevent an inadvertent injury would benefit patients.

Another common problem is disturbance of IV lines, pulse oximetry wires and blood pressure apparatus on the upper extremity by the operating surgeon.

The hand and arm protector of the present invention prevents against certain kinds of crushing injury by keeping the hands and arms of a patient pulled into the sides and protected. The protector is also designed to prevent a surgeon from leaning directly against an arm and causing problems with the IV tubing, wires and blood pressure cuffs. The invention is simple to place into operation and reusable. The weight of the patient helps to anchor the base.

SUMMARY OF THE INVENTION

The invention comprises a hand and arm protector in which a base portion of the protector is attached to an elongated arm protection channel. The arm channel is anticipated to have a length of approximately one to three feet and a height above the base of approximately three to ten inches. Such dimensions would accommodate design choices, variations in the sizes of arms and should permit the containment of at least the elbow and forearm of a patient. The arm channel terminates longitudinally in a mitt. The mitt preferably has at least semi-rigid means, if not rigid means, for limiting movement of the hand and fingers in the longitudinal direction. Preferably, the mitt limits movement of the hand and fingers in the downward direction also, and the rigid or semi-rigid shape prevents crushing of the hand from above.

In preferred embodiments of the hand and arm protector, the base, channel and mitt are molded into a unitary piece of high impact plastic. Also, in preferred embodiments, the arm protection channel would contain gel pads attached to portions of its surface, much as in Allen stirrups, to prevent nerve compression injuries.

The invention also comprises a method for protecting hands and arms during surgery and in particular during pelvic laparoscopy, cystoscopy, colorectal and vulvovaginal surgery. The method includes placing the base of a hand and arm protector under a patient. The arm of the patient is placed within an arm protection channel of the protector such that a portion of the channel encompasses at least a portion of the outside of the arm. A hand of the patient is placed into a mitt attached to one end of the arm protection channel. The mitt encompasses at least the extremities of the hand.

BRIEF DESCRIPTION OF THE DRAWINGS

FIG. 1 illustrates a plan view of an operating table that contains a left and right embodiment of the present invention.

FIG. 2 illustrates the embodiment of FIG. 1 wherein the inside surfaces of the embodiment are shown covered with a gel pad.

FIG. 3 comprises a cross-sectional view along the indicated lines of FIG. 2, illustrating in particular the gel pad within the mitt portion of the device.

FIG. 4 comprises a cross-sectional view along the indicated lines of FIG. 2, illustrating in particular the gel pad within the channel at the location of the groove for accommodating a patient's elbow.

A better understanding of the present invention can be obtained when the following detailed description of the preferred embodiment is considered in conjunction with the following drawings.

DESCRIPTION OF THE PREFERRED EMBODIMENTS

FIG. 1 illustrates two hand and arm protectors P located on operating table T. One protector is for the left arm and the other protector is for the right arm. The protectors are separate units. They are not connected directly to the table. Rather, they are designed to fit under a patient and over the mattress and sheets.

Each protector P is comprised of a base B attached to an elongated arm protection channel C that terminates longitudinally in a mitt M. The protector of FIG. 1 is illustrated as if the base, channel and mitt were molded into a unitary piece of material such as a high impact plastic.

Area 10 of FIG. 1 illustrates where the patient's head would be situated on the operating table. Table T is shown hinged by hinges H with the lower portion of the table dropped. It is clear that if the patient's arms and hands were not protected, the patient's hands might extend to space 12 between the upper and lower portions of hinged table T. When the lower portion of table T is hinged upward, as at the end of a procedure, without suitable hand protection means the patient's hands could be crushed.

L defines a longitudinal direction with respect to an operating table with protectors P in place. It is envisioned that channel C of protector P would extend longitudinally from approximately one to three feet. Such length should enable the protector to protect significant portions of most patient's arms, such as the elbows and forearms. Channel C is envisioned to also extend upward from base B by approximately three to ten inches. With such extension upward channel C should protect most patient's arms from being pressed or crushed by doctors and medical personnel leaning over the sides of operating table T.

Channel C terminates longitudinally in mitt M. Various types of restraining mitts are known in the art. Mitt M of the illustrated embodiment comprises a semi-spherical and basically rigid shell into which the patient's hand is placed. Such shell, as illustrated, protects the patient's hand from crushing injury in several directions, including importantly the longitudinal direction L and the downward direction into operating table T, which directions or combinations of direction may involve space 12.

The preferred embodiment of the present invention shows the base, channel and mitt molded into one piece from a basically rigid material, such as a high impact plastic. However, many different types of base arrangements would be known to also function adequately by one of skill in the art. The base of the preferred embodiment anchors channel C and mitt M by using the weight of the patient. Such is convenient, but not necessary. The base need not be solid, and it need not be molded of one piece with the channel. Again, any suitable base that performs the anchoring function is adequate.

Likewise, channel C is shown with curved sides. However, channel C could have straight sides or sides with less regular shapes. Also, channel C need not be solid. It could be comprised of a plurality of structural pieces.

Mitt M in the preferred embodiment is shown totally enclosing most of the hand and wrist. However, it is only necessary that mitt M has sufficient structure to protect the hand inserted from escape into the area 12 of operating table T.

In preferred embodiments it is envisioned that inside portions of channel C would have a groove in which at least the forearm and elbow of the patient could rest, preferably padded with gel pads like those found in the Allen stirrups, to prevent nerve compression injuries. The preferred embodiment is also anticipated to be designed such that there would be sufficient room for the forearms of obese patients to fit.

FIGS. 2 and 3 illustrate gel pad or pads G attached to the inner surface of the protector. In the embodiment of FIGS. 2 and 3 gel pad G is attached to the entire inner surface of the device. Preferably, the gel pad covers all of the interior surfaces and is removable for easy washability. FIG. 3 offers a cross-sectional representation of mitt portion M illustrating hard plastic shell area C of channel C and of the mitt and gel pad area G.

FIG. 4 shows a cross-sectional view along the indicated lines of FIG. 2. The gel pad is shown within the channel at the location of the groove in order to accommodate the patient' arm.

In operation, the flat extension or base portion of protector P would be tucked under a patient's back to anchor the protector with arm channel and hand mitt to one side of the patient on a table. The protector is envisioned as placed under the patient but on top of the mattress and sheets. An arm of the patient would be placed within the arm channel of the protector so that a portion of the channel encompasses or protects at least a portion of the outside of the arm. Preferably this includes the forearm and elbow. The hand of the patient would be placed in the mitt located at the termination of one end of the arm channel. Thus, the patient is comfortable. The patient's arms are protected from being pressed by the surgeon leaning over the operating table, which leaning against the arm might also cause problems with IV tubing, wires and blood pressure cuffs. In such a position the mitt protects the patient's fingers from being mangled or amputated if a hinged table is straightened out at the end of the procedure. Use of such method helps avoid unnecessary disturbance of IV lines, pulse oximetry wires and blood pressure apparatus on the patient's upper extremity by the operating surgeon.

The foregoing disclosure and description of the invention are illustrative and explanatory thereof. Various changes in the size, shape and materials as well as the details of the illustrated construction may be made without departing from the spirit of the invention.

I claim:

1. An apparatus for protecting a patient's hand and arm from injury while the patient is lying on a treatment table, the apparatus comprising:

a base for placement under the patient's torso, the base having a side medial to the patient and a side lateral to the patient;

a channel member extending upwardly from said lateral side of said base, said channel member extending longitudinally from an upper end along said lateral side of said base for protecting a portion of the patient's arm; and a mitt formed at a lower end of said channel member, said mitt enclosing at least the fingers of the patient's hand and protecting same, said base, channel member, and mitt being integrally formed of a unitary, piece of a rigid material.

2. The apparatus of claim 1, further comprising a groove in the channel member for accommodating the patient's forearm and elbow.

3. The apparatus of claim 1, further comprising padding in said channel member.

4. The apparatus of claim 1, formed of a unitary piece of high impact plastic.

5. A method for protecting a patient's hand and arm while the patient is lying on a treatment table comprising:

placing the base of the apparatus of claim 1 under a portion of the patient's torso between the patient and a treatment table;

placing the patient's arm in the channel member of the apparatus; and placing the patient's hand in the mitt of the apparatus.

\* \* \* \* \*